United States Patent [19]
Nakanishi et al.

[11] Patent Number: 5,952,308
[45] Date of Patent: Sep. 14, 1999

[54] MINERAL ABSORPTION PROMOTING AGENT

[75] Inventors: Noboru Nakanishi; Yoshio Kitada, both of Yokohama, Japan

[73] Assignee: Pola Chemical Industries Inc., Shizuoka, Japan

[21] Appl. No.: 07/919,543

[22] Filed: Jul. 24, 1992

[30] Foreign Application Priority Data

Jul. 29, 1991 [JP] Japan ................................. 3-188827
Jun. 30, 1992 [JP] Japan ................................. 4-173025

[51] Int. Cl.$^6$ ..................... A01N 43/04; C07H 15/04; C07H 23/00
[52] U.S. Cl. ........................ 514/25; 536/120; 536/121
[58] Field of Search ................ 536/121, 120; 514/25

[56] References Cited

U.S. PATENT DOCUMENTS

| | | | |
|---|---|---|---|
| 3,275,514 | 9/1966 | Saltman et al. | 536/121 |
| 4,225,592 | 9/1980 | Lakatos et al. | 536/121 |
| 4,689,322 | 8/1987 | Kulbe et al. | 536/121 |

FOREIGN PATENT DOCUMENTS 59-42683  10/1984  Japan .

OTHER PUBLICATIONS

Yakugaku Zasshi, 90, 120–126 (1970).
Yakugaku Zasshi, 90, 1480–1487 (1970).
Chemical Abstract, 60 5287f (1992).
*The Merck Index, 11$^{th}$ Edition*, Susan Budavari, editor, entry # 9798, 4242, 5632, and 4360.

*Primary Examiner*—D. Margaret Mach
*Attorney, Agent, or Firm*—Dike, Bronstein, Roberts & Cushman, LLP; David G. Conlin; George W. Neuner

[57] ABSTRACT

A mineral absorption promoting agent containing oligouronic acid, e. g. oligogalacturonic acid or oligomannuronic acid [degree of polymerization (n)=1 to 9] is described. Since this oligouronic acid [polymerization degree (n)=1 to 9] forms a complex with mineral, it promotes absorption of minerals into living organisms by simply adding it to foods, drinks or pharmacentical compositions for oral use. Since the agent has no problem with safety, the agent is suitable for repeated eating, drinking or taking, and the agent is very effective.

10 Claims, No Drawings

MINERAL ABSORPTION PROMOTING AGENT

BACKGROUND OF THE INVENTION

1. Field of the Invention

The present invention relates to a mineral absorption promoting agent, and in particular to a mineral absorption promoting agent containing oligouronic acid [degree of polymerization (n)=1 to 9], which promotes absorption of minerals such as iron, calcium, etc. into living organisms.

2. Description of the Prior Art

In recent years, it has become increasingly difficult to take minerals from foods because of propagation of refined and sophisticated food products, meals with imbalanced nutrition and irregular eating habits. For this reason, in order to supply constituents or activators of numerous enzyme systems, which are essential elements such as calcium, magnesium, potassium, zinc, manganese, copper, iron, etc. indispensable for the normal function of living organisms, it has been proposed to utilize complexes or conjugates of these essential elements.

For example, chondroitin sulfate-iron(II)-iron(III), algin-iron(II)-iron(III), and pectin-iron(II)-iron(III) have been reported as such substances [Japanese Patent Examined Publication No. 44-2802, Yakugaku Zasshi (Journal of Pharmaceutical Science), 90, 120–126 (1970); Yakugaku Zasshi (Journal of Pharmaceutical Science), 90, 1480–1487 (1970); Chemical Abstract, 60, 5287 f.; Belgian Patent Specifications Nos. 619,267 and 652,508]. Metal ion complexes of oligogalacturonic acids or polygalacturonic acids also have been reported as such substances (Japanese Patent Examined Publication No. 59-42683).

Since the above complexes or conjugates of algin-iron (II)-iron(III), pectin-iron(II)-iron(III) and degraded casein-iron(II)-iron(III) are chemically undefined, the metal complexes which have reproducible quality and reproducible biological effects are not obtainable.

Though metal ion complexes of oligogalacturonic acid or polygalacturonic acid have reproducible quality and reproducible biological effects, they are relatively macromolecular substances with polymerization degree (n) of 10 to 145, and are not easily absorbed into living organisms.

In particular, the deficiency of iron or calcium may cause anemia or osteoporosis, and there are now strong demands for foodstuffs and medical drug preparations which can be ingested efficiently.

SUMMARY OF THE INVENTION

The present inventors have been studying the usefulness of known metal complexes of oligogalacturonic acid or polygalacturonic acid [polymerization degree (n)=10 to 145], and have found that metal complexes of oligogalacturonic acid [polymerization degree (n)=2 to 9] have higher absorbing property than the metal complexes of oligogalacturonic acid of 10 or more of polymerization degree (n). Further the present inventors have found that absorbing mechanisms through an intestinal tract are different from each other in these two kinds of complexes. The present inventors have found a fast acting pharmaceutical agent which contains a complex of hydrolyte of pectin (n=2 to 9) and metal and which has high absorbing ratio into living organisms. As a result of further studying absorption of minerals into living organisms, the present inventors have found that oligouronic acid (n=1 to 9) reacts with minerals in foods and drinks and promotes absorption of the minerals into living organisms without previously making a metal complex, and finally completed the present invention.

Specifically, the present invention relates to a mineral absorption promoting agent containing oligouronic acid [polymerization degree (n)=1 to 9].

The oligouronic acids include an oligogalacturonic acid which is a hydrolyte of pectin; an oligomannuronic acid which is a hydrolyte of alginic acid; and an oligoglucuronic acid which is a degraded product of gum arabic. The oligouronic acid includes a monomer (n=1).

In the present invention, pectin for obtaining oligogalacturonic acid may be derived from any raw material. Such raw materials include apples, lemons, beets, sunflowers, etc. Main component of the pectin is polygalacturonic acid.

The hydrolysis of pectin may be conducted by enzymatic or chemical hydrolysis. Hydrolases include protopectinase, polygalacturonase, etc. For chemical hydrolysis, acid or alkali may be used.

The hydrolyte of pectin of the present invention is mainly consisted of oligo- or polygalacturonic acid with 1 to 9 of polymerization degree.

Raw materials for oligomannuronic acid include alginic acid, and the acid may be hydrolyzed by chemical or enzymatic hydrolysis. For chemical hydrolysis, acid or alkali may be used.

Liquid composition of oligouronic acid just after hydrolysis can be used with the same efficacy as the oligouronic acid purified by chromatography or filtration. Oligouronic acid is abundantly found in fruits and seaweeds, and its safety is assured from long eating history of mankind.

According to the present invention, oligouronic acid is added to foodstuffs or pharmacentical compositions for oral use, which contain minerals such as iron, calcium, copper, cobalt, magnesium, potassium, manganese, zinc, chromium, molybdenum, vanadium, nickel, etc. or mixture of these substances. Through preparation process or eating process of these foods and drinks, oligouronic acid and minerals such as metals form a complex, and the complex is absorbed in living organisms in stable form.

The metal complexes of the oligouronic acid, for example, the complex obtained through reaction of oligogalacturonic acid [polymerization degree (n)=1 to 9], which is a hydrolyte of pectin with iron, calcium, copper, cobalt, etc. is a metal iron complexes of oligogalacturonic acid or polygalacturonic acid having the following formula:

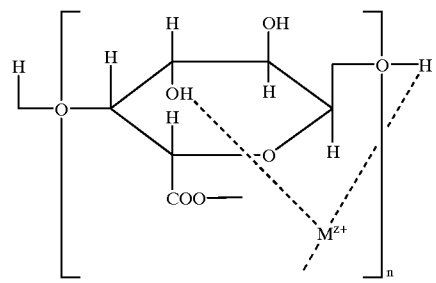

(wherein n is an integer from 1 to 9; M represents at least a type of metal cation selected from iron(II), iron(III), calcium (II), copper(II), magnesium(II), potassium(I), cobalt(II), manganese(II), zinc(II), chromium(III), molybdenum(V), vanadium(IV) and nickel(II); and z is an integer, corresponding to the charge or valence number of the metal atom.)

The minerals contained in foods and drinks are normally present in state of salts or complexes in iron and/or calcium. Iron may be as ferric pyrophosphate, ferric chloride, ferrous sulfate, iron succinate, ferrous sodium succinate, etc., and calcium may be as calcium chloride, calcium lactate, calcium gluconate, etc.

In the mineral absorption promoting agent according to the present invention, oligouronic acid can mixed with any type of foods containing minerals and can be added to any food product when eating. The mixing or adding promotes absorption of the minerals in foods and drinks into living organisms.

The mineral absorption promoting agent containing oligouronic acid can be used as a pharmaceutical agent for oral use or parenteral use. For oral use, powder, tablet, emulsion, capsule, granule and liquid preparation may be cited as well as the foods and drinks containing the mineral absorption promoting agent.

As vehicles, those already known in this field are used. For example, vehicles for powder preparation and other powder preparation for intestinal use, include lactose, starch, dextrin, calcium phosphate, calcium carbonate, synthetic and natural aluminum silicate, magnesium oxide, dried aluminum hydroxide, magnesium stearate, sodium bicarbonate, etc. Vehicles for liquid preparation, include water, glycerine, propyleneglycol, simple syrup, ethanol, fatty oil, ethyleneglycol, polyethyleneglycol, sorbitol, etc.

The mineral absorption promoting agent may be preferably added to foods and drinks 0.1 to 10% by weight.

Oligouronic acid [polymerization degree (n)=1 to 9] is easily combined with various types of minerals to form a complex. The complex thus produced is thermally stable and stably dissolved in wide pH range from acid to alkaline conditions and is easily absorbed into living organisms. Therefore, by simply adding oligouronic acid to foods and drinks containing minerals, the minerals can be easily absorbed into living organisms without previously forming a complex.

DESCRIPTION OF THE PREFERRED EMBODIMENTS

EXAMPLES

The present invention will be described in more detail with the following examples. The following examples are given to illustrate embodiments of the present invention as it is presently preferred to practice. It will be understood that the examples are illustrative, and that the invention is not to be considered as restricted except as indicated in the claims.

1. Preparation of oligouronic acid.

(1) Preparation method of oligogalacturonic acid from apple pectin

To 1,000 g of a 5% aqueous solution of apple pectin, 5 g of a commercial pectinase preparation was added, and the mixture was agitated for 3 hours at 35° C. and was subjected to an enzymatic treatment. The resulting solution was centrifuged at 3,500 rpm for 10 minutes. By removing the insoluble substances, 980 g of the supernatant was obtained. This supernatant was filtered through ultrafiltration membrane with molecular weight of 3,000, and 920 g of the filtrate thus obtained was further freeze-dried to prepare 38 g of powder.

Main component of this powder was oligogalacturonic acid with 6 of degree of polymerization.

(2) Preparation method of oligomannuronic acid from alginic acid

To 3,000 g of a 1% aqueous solution of alginic acid prepared by heating, 1N NaOH solution was dropped to reach pH 8, and the mixture was heated at 90° C. under atomspheric pressure for one hour to be subjected to alkali hydrolysis.

The resulting solution was cooled to room temperature and was neutralized with 0.5N HCl solution. The resulting solution was further condensed at 60° C. under reduced pressure, and 160 g of condensed solution was obtained.

Soluble solid content in this condensed solution was 18%, and main component was oligomannuronic acid with 4 of degree of polymerization.

(3) Preparation method of galacturonic acid from citrus pectin

To 500 g of a 8% aqueous solution of pectin derived from citrus such as grapefruits and lemons, 3 g of a commercial pectinase preparation was added, and the mixture was agitated for 2 hours at 40° C. and was subjected to the enzymatic treatment. The resulting solution was continued to be agitated for one hour and was filtered through an ultrafiltration membrane with 50,000 cut to obtain 470 g of filtrate. The filtrate contains about 33 g of galacturonic acid.

2. Mineral absorption promoting effect of oligouronic acid (1) Mineral absorption promoting effect test on animals Wistar male rats (body weight:80 g) were feeded for 3 weeks, giving iron-free feed, ferrous sulfate-added feed (iron: 12 ppm), or ferrous sulfate and oligogalacturonic acid-added feed (iron: 12 ppm, powder oligogalacturonic acid obtained in the preparation method 1=0.5%).

During the period, hemoglobin concentration in blood was measured every 7 days, and utilization ratios of iron in each of these feeds were compared, using hemoglobin increase (hemoglobin concentration in blood×blood volume) as an index.

TABLE

Net increase of hemoglobin (number of tested rats = 10); unit: g ± SD

| Feed | At start | 7th day | 14th day | 21st day | Utilization ratio |
|---|---|---|---|---|---|
| Iron-free | 0 | 0.1 | 0 | 0 | — |
| Ferrous sulfate-added | 0 | 0.2 ± 0.1 | 0.3 ± 0.1 | 0.4 ± 0.2 | 33% |
| Ferrous sulfate + Oligogalacturonic acid-added | 0 | 0.3 ± 0.1 | 0.7 ± 0.2 | 1.1 ± 0.2 | 97% |

Addition of oligogalacturonic acid to the feed, as obvious from the table, increased significantly the utilization ratio of ferrous sulfate in the feed as well as hemoglobin value.

(2) Mineral absorption effect test by artificial gastric juice

Twenty (20) g of Ferrous sulfate+oligogalacturonic acid-added feed which was used in the above animal test was added to each of 200 g of artificial gastric juice and artificial intestinal juice (as per Japanese Pharmacopeia), and the mixtures were agitated at 37° C. for one hour.

Each of these mixtures was filtered, and iron in the filtrate was assayed. About 100% of the iron in the feed was moved to liquid phase.

Moreover, iron was combined with oligogalacturonic acid, and the filtrate was found not to be decomposed even when heated at 95° C. for 15 minutes.

3. Formation of calcium-oligomannuronic acid in yogurt

To 100 g of commercial liquid yogurt, 4 g of oligomannuronic acid syrup (18%) as obtained in the above preparation method was added, and the mixture was agitated for 10 minutes.

Then, a part of the agitated mixture was diluted by 10 times with water and was centrifuged at 3500 rpm, for 10 minutes. After removing insoluble substances, calcium in the supernatant was assayed.

As a result, calcium was found to be combined with oligomannuronic acid and stably dissolved, although most of calcium in yogurt is usually present as calcium lactate.

4. Safety of oligouronic acid

| Acute toxicity test of oligogalacturonic acid | | |
|---|---|---|
| Animal: | Wistar rat: One group comprising 10 each of male and female rats | |
| Specimen: | 50% oligogalacturonic acid aqueous solution | |
| Administration: | Oral forced administration | |
| Dosage: | Group 1 | 10 ml/kg |
| | Group 2 | 20 ml/kg |
| | Group 3 | Control |

Death occurred in none of the groups, and $LD_{50}$ was not obtained. There was no abnormal sign in autopsy after 14 days.

5. Examples of oligouronic acid preparations

| (1) Oligogalacturonic acid syrup | |
|---|---|
| Oligogalacturonic acid powder (preparation method 1) | 20% |
| Starch syrup | 50% |
| Glucose | 7% |
| Sucrose ester | 3% |
| Water | 20% |
| | 100% |

| (2) Oligomannuronic acid powder | |
|---|---|
| Oligomannuronic acid powder (Preparation method 2) | 10% |
| Lactose | 50% |
| Dextrin | 30% |
| Corn starch | 5% |
| Sucrose ester | 5% |
| | 100% |

6. Blending example of oligouronic acid to foods and drinks

| (1) Candy blended with iron and oligogalacturonic acid | |
|---|---|
| Sugar | 50% |
| Starch syrup | 42% |
| Oligogalacturonic acid powder (preparation method 1) | 5% |
| Sour seasoner | 2% |
| Flavor | 0.5% |
| Coloring agent | 0.3% |
| Ferric pyrophosphate | 0.2% |
| | 100% |

| (2) Milk added with oligogalacturonic acid | |
|---|---|
| Milk | 90% |
| Sugar | 8% |
| Oligogalacturonic acid syrup | 2% |
| | 100% |

(3) Tablet mixed with calcium and oligomannuronic acid

| (3) Tablet mixed with calcium and oligomannuronic acid | |
|---|---|
| Sugar | 60% |
| Lactose | 20% |
| Sucrose ester | 5% |
| Yogurt powder | 5% |
| Cow bone powder | 5% |
| Oligomannuronic acid powder (preparation method 2) | 3% |
| Flavor | 2% |
| | 100% |

The mineral absorption promoting agent containing oligouronic acid [degree of polymerization (n)=1 to 9] according to the present invention combines with minerals and is useful as an agent to promote absorption of the minerals into living organisms. The agent can promote absorption of minerals into living organisms even when a mineral compound is not in specific state. For example, by simply adding oligouronic acid to foods and drinks or pharmacentrical composition preparations for oral use, a complex is prepared, which makes minerals in the foods, drinks, etc. easily absorbable into living organisms and can promote absorption of minerals into living organisms. There is no problem with safety, and the agent can be repeatedly eaten, drunk or taken.

What is claimed is:

1. A consumable composition comprising a foodstuff and a mineral absorption promoting agent which consists essentially of oligouronic acid with a degree of polymerization from n=1 to n=9.

2. The consumable composition of claim 1, wherein the oligouronic acid is present in an amount of 0.1 to 10% by weight.

3. The consumable composition of claim 1, wherein the oligouronic acid is selected from oligogalacturonic acid, oligomannuronic acid or oligoglucuronic acid.

4. The consumable composition of claim 3, wherein the oligouronic acid is present in an amount of 0.1 to 10% by weight.

5. A pharmaceutical composition comprising a pharmaceutically acceptable vehicle containing a mineral absorption promoting agent which consists essentially of oligouronic acid with a degree of polymerization from n=1 to n=9.

6. The pharmaceutical composition of claim 5, wherein the oligouronic acid is selected from oligogalacturonic acid, oligomannuronic acid or oligoglucuronic acid.

7. The pharmaceutical composition of claim 5, which is for oral or parenteral use.

8. The pharmaceutical composition of claim 5, wherein the composition further contains a mineral.

9. The pharmaceutical composition of claim 8, wherein the mineral is iron, calcium, or both.

10. The pharmaceutical composition of claim 9, wherein the iron is a trivalent compound.

* * * * *